United States Patent
Zhao et al.

(10) Patent No.: US 9,284,293 B2
(45) Date of Patent: Mar. 15, 2016

(54) REACTIVE RECOVERY OF DIMETHYL CARBONATE FROM DIMETHYL CARBONATE/METHANOL MIXTURES

(75) Inventors: Haibo Zhao, The Woodlands, TX (US); Mark Posey, Spring, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 0 days.

(21) Appl. No.: 13/819,373

(22) PCT Filed: Aug. 19, 2011

(86) PCT No.: PCT/US2011/048369
§ 371 (c)(1),
(2), (4) Date: Feb. 27, 2013

(87) PCT Pub. No.: WO2012/030554
PCT Pub. Date: Mar. 8, 2012

(65) Prior Publication Data
US 2013/0165669 A1    Jun. 27, 2013

Related U.S. Application Data

(60) Provisional application No. 61/379,145, filed on Sep. 1, 2010.

(51) Int. Cl.
*C07D 317/36* (2006.01)
*C07C 269/04* (2006.01)
*C07D 317/38* (2006.01)
*C07C 68/06* (2006.01)

(52) U.S. Cl.
CPC .............. *C07D 317/36* (2013.01); *C07C 68/06* (2013.01); *C07C 269/04* (2013.01); *C07D 317/38* (2013.01)

(58) Field of Classification Search
CPC .. C07D 317/36; C07D 317/38; C07C 269/04; C07C 68/06
USPC ........................................................ 549/230
See application file for complete search history.

(56) References Cited

U.S. PATENT DOCUMENTS

| 5,191,123 | A | 3/1993 | King |
| 5,292,917 | A | 3/1994 | Nishihira |
| 5,463,109 | A * | 10/1995 | Nishihira et al. .............. 560/157 |
| 6,315,868 | B1 | 11/2001 | Nisoli |
| 2009/0203933 | A1 | 8/2009 | Ryu |
| 2010/0158835 | A1 | 6/2010 | Bandres et al. |
| 2010/0209979 | A1 | 8/2010 | Jung et al. |

FOREIGN PATENT DOCUMENTS

| CN | 1631871 A | 6/2005 |
| WO | 2009/035269 A | 3/2009 |

OTHER PUBLICATIONS

Rokicki, G., Hyperbranched aliphatic polyethers obtained from environmentally benignmonomer: glycerol carbonate, 2005, 7, 529-539.*
Li, J., Coupling reaction and azeotropic distillation for the synthesis of glycerol carbonate from glycerol and dimethyl carbonate, 2010, Chem. Engin. Proc. 49, 530-535.*
IUPAC Compendium of Chemical Terminology—the Gold Book; Copyright © 2005-2014 International Union of Pure and Applied Chemistry; accessed online Mar. 18, 2015; http://goldbook.iupac.org/about.html.; excerpt p. 1.*
Nicole Fricke, et al. "Carbonate Couplers and Functional CYclic Carbonates from Amino Acids and Glucosamine" Macromolecular Chemistry and Physics, vol. 210, No. 3-4, Feb. 20, 2009, pp. 242-255.

* cited by examiner

*Primary Examiner* — Samantha Shterengarts
*Assistant Examiner* — Matt Mauro
(74) *Attorney, Agent, or Firm* — Huntsman International LLC

(57) ABSTRACT

A method of producing a carbonate product including mixing a DMC and methanol mixture with an alcohol, reacting the DMC with the alcohol to form carbonate product, and removing a substantial portion of unreacted DMC and methanol. In one embodiment, the method may be repeated to reach a desired alcohol conversion by adding more DMC and methanol mixture.

22 Claims, 1 Drawing Sheet

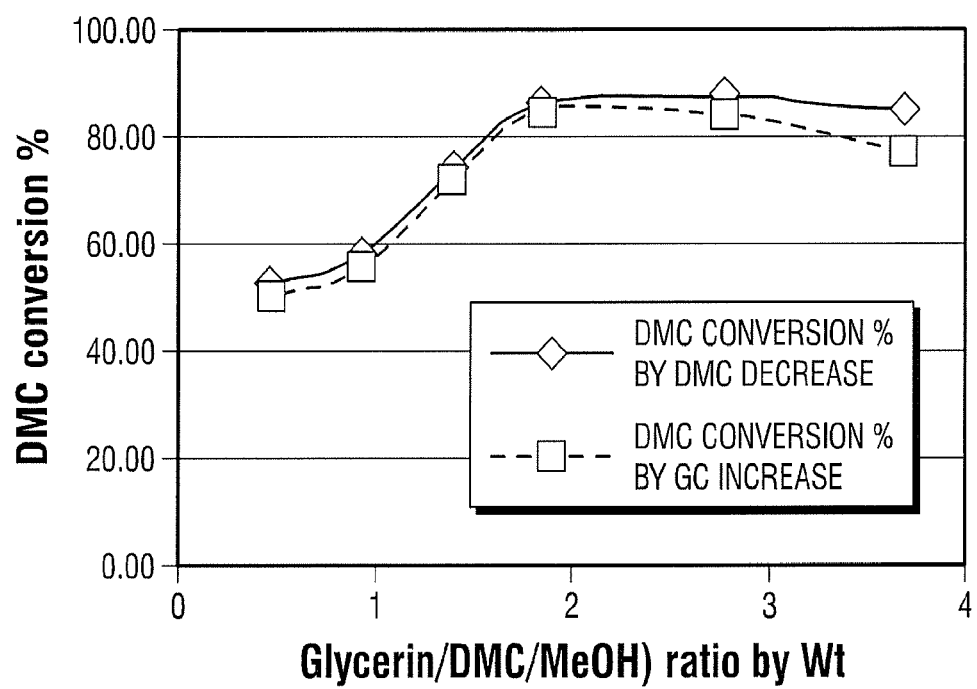

REACTIVE RECOVERY OF DIMETHYL CARBONATE FROM DIMETHYL CARBONATE/METHANOL MIXTURES

CROSS-REFERENCE TO RELATED APPLICATION

This application claims priority to U.S. Pat. App. Ser. No. 61/379,145 filed Sep. 1, 2010 which is incorporated herein by reference.

BACKGROUND OF THE INVENTION

1. Field of the Invention

Embodiments of the present invention generally relate to a process for using a dimethyl carbonate and methanol mixture. In particular, embodiments of the present invention relate a process of using a dimethyl carbonate and methanol azeotropic mixture. In particular still, embodiments of the present invention relate to a process of using a dimethyl carbonate mixture in a reaction to produce a carbonate.

2. Description of the Related Art

Dimethyl carbonate (also referred to herein as "DMC") is useful as a starting material in the synthesis of carbonates and polycarbonates. Dimethyl carbonate is often present in a mixture with methanol. In various processes to produce carbonates, dimethyl carbonate is often obtained in a mixture with methanol. The mixture of dimethyl carbonate and methanol form an azeotropic composition when the composition includes approximately 70 wt % methanol and 30 wt % DMC at atmospheric pressure.

Various processes have been proposed to separate the azeotropic mixture and reuse the DMC. Known processes for separating the azeotropic mixture of dimethyl carbonate and methanol include extractive distillation, membrane separation, and pressure distillation.

In an extractive distillation process, an extractive agent is added to the mixture of components to be separated in the distillation process. The addition of the extractive agent changes the relative volatilities of the components of the mixture. The relative volatilities are changed sufficiently to allow effective separation by distillation. For example, U.S. Pat. No. 5,292,917 discloses a process for the extractive distillation of a dimethyl carbonate/methanol mixture by distilling the mixture in the presence of dimethyl oxalate. Two distillation columns are used in series to separate the dimethyl carbonate from the methanol. In the first column, methanol is removed at the top of the column, and the dimethyl carbonate/dimethyl oxalate mixture is fed to the second column. In the second column, the dimethyl carbonate is separated from the dimethyl oxalate.

Membranes have also been proposed for the separation of methanol and DMC. However, the purity of the streams obtained do not always justify the expense of the separation and in many cases still require some sort of distillation.

Pressure distillation can be used to lower the DMC concentration in the azeotrope. However, a pressure of 150 psig is typically needed to sufficiently break the azeotrope. Columns rated at 150 psig operating pressure are not as common as low pressure or vacuum towers. It is also not typical to find a pressure tower attached to a batch reactor.

There is a need, therefore, for a simpler and more economical process for utilizing a dimethyl carbonate and methanol mixture. There is also a need for a process for using the dimethyl carbonate and methanol mixture as a reactant to produce a desired product, such as a carbonate or carbamate.

SUMMARY OF THE INVENTION

The present invention generally relates to a process for utilizing a DMC/methanol mixture directly in a reaction to produce a desired product. In this respect, the effort and expense necessary to separate a potentially azeotropic mixture may be avoided.

In one embodiment, the DMC/methanol mixture is reacted with alcohols, diols, triols, polyols or amines. The reaction converts the DMC in the DMC/methanol mixture to carbonates, polycarbonates, or carbamates. The light components, including methanol, from the reaction are removed by distillation, flash distillation, or stripping. The undistilled portion contains the desired carbonates, polycarbonates, or carbamates. In another embodiment, the undistilled portion may act as a precursor mixture to the desired final product. In yet another embodiment, the undistilled portion may optionally be reacted with additional amounts of the DMC/methanol mixture to further improve the yield of the desired carbonates, polycarbonates, or carbamates. In yet another embodiment, the undistilled portion may optionally be reacted with pure DMC to make the desired final product. Because some DMC in the DMC/methanol azeotropic mixture was utilized, the pure DMC required in the following step was reduced. The product yield relative to DMC and the economics of the DMC-based chemistry are thus improved.

In one embodiment, a method of producing a carbonate includes mixing a DMC and methanol composition having 20% to 80% DMC by weight with an alcohol having 2 to 15 carbon atoms; reacting the DMC with the alcohol to form a carbonate product; and removing a substantial portion of unreacted DMC and methanol, thereby forming a product composition containing the carbonate product. In another embodiment, the method optionally includes mixing an additional amount of DMC and methanol composition having 20% to 80% DMC by weight with the product composition and removing a substantial portion of unreacted DMC and methanol, thereby forming a second product composition. The steps of adding and reacting with additional amounts of DMC and methanol composition and removing unreacted DMC and methanol may be repeated until the desired product composition is achieved. In yet another embodiment, the method optionally includes mixing an at least 95% by weight of DMC composition with the second product composition. In yet another embodiment, the product composition includes less than 10% by weight of DMC or methanol.

In one embodiment, the process includes reacting glycerine with a DMC/methanol mixture to produce a product composition containing glycerine carbonate. The process also includes removing the light component such as methanol and DMC from the product composition. The product composition may optionally be reacted with additional DMC/methanol mixture in a second reaction. Optionally, additional reactions, such as a third reaction or a fourth reaction, with additional DMC/methanol mixture may be performed. The product composition optionally may be reacted with pure DMC to achieve the desired reaction conversion.

In another embodiment, a method of producing a carbamate includes mixing a DMC and methanol composition having 20% to 80% DMC by weight with an amine; reacting the DMC with the amine to form a carbamate product; and removing a substantial portion of unreacted DMC and methanol, thereby forming a product composition containing the carbamate product.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

FIG. 1 shows the effect of changing the weight ratio of glycerine to the DMC/methanol mixture have on DMC conversion.

DETAILED DESCRIPTION

A method of producing a carbonate product by mixing a DMC and methanol mixture with an alcohol, reacting the DMC with the alcohol to form a carbonate product, and removing a substantial portion of unreacted DMC and methanol. In one embodiment, the method may be repeated to reach a desired alcohol conversion by adding more DMC and methanol mixture. In another embodiment, pure DMC may be added and reacted with the product composition to achieve the desired alcohol conversion.

In one embodiment, the DMC/methanol mixture is reacted with alcohols, diols, triols, polyols or amines. The reaction converts the DMC in the DMC/methanol mixture to carbonates, polycarbonates, or carbamates. The light components, including methanol, from the reaction are removed by distillation, flash distillation, or stripping. The undistilled portion contains the desired carbonates, polycarbonates, or carbamates. In another embodiment, the undistilled portion may act as a precursor mixture to the desired final product. In yet another embodiment, the undistilled portion may optionally be reacted with additional amounts of the DMC/methanol mixture to further improve the yield of the desired carbonates, polycarbonates, or carbamates. In yet another embodiment, the undistilled portion may optionally be reacted with pure DMC to make the desired final product.

The DMC/methanol mixture for the reaction may include about 20% to 80% by weight of DMC; preferably about 30% to 70% by weight of DMC; more preferably about 40% to 50% by weight of DMC. Thus, embodiments disclosed herein are not limited to azeotropic DMC/methanol compositions. The DMC/methanol mixture may be supplied from any suitable source. In one embodiment, the DMC/methanol mixture is purchased from a vendor. In another embodiment, the DMC/methanol mixture is a product stream of another reaction and the mixture may be used make carbonates. In this respect, the reaction may advantageously use the existing equipment to perform the reaction process.

Suitable alcohols include aliphatic or aromatic alcohols having an alkyl group having 2 to 15 carbon atoms or an alkyl aryl group having 6 to 15 carbon atoms. Examples of an alkyl group include ethyl, propyl, butyl, pentyl, hexyl, decyl, and cyclohexylmethyl; and an alkyl aryl group such as benzyl and alkyl benzyl. The above-mentioned alkyl groups and alkyl aryl groups may be substituted with other substituents such as lower alkyl group and may also contain an unsaturated bond therein. In one example, diethyl carbonate can be made from reacting ethanol with the DMC/methanol mixture. In another example, di-n-butyl carbonate can be made from reacting n-butanol with the DMC/methanol mixture. In yet another example, diphenyl carbonate can be made from reacting phenol with the DMC/methanol mixture. In yet another example, cyclic butylene carbonate can be made from reacting 1,2-butylene glycol with the DMC/methanol mixture.

Suitable alcohols also include diols, triols, and other polyols having an alkyl group having 2 to 15 carbon atoms or an alkyl aryl group having 6 to 15 carbon atoms. Examples of diols include ethylene glycol, propylene glycol, butylene glycol, and dihydroxy benzene. An exemplary triol is glycerine. The above-mentioned alkyl groups and alkyl aryl groups may be substituted with other substituents such as lower alkyl group and may also contain an unsaturated bond therein. In one example, ethylene carbonate can be made from reacting ethylene glycol with the DMC/methanol mixture. In another example, propylene carbonate can be made from reacting propylene glycol with the DMC/methanol mixture. In yet another example, glycerine carbonate can be made from reacting glycerine with the DMC/methanol mixture.

Suitable amines include ammonia and aliphatic and aromatic amines. Suitable amines may include an alkyl group such as ethyl, propyl, butyl, pentyl, hexyl, decyl, and cyclohexylmethyl; and/or an alkyl aryl group such as benzyl and alkyl benzyl. The above-mentioned alkyl groups and alkyl aryl groups may include 2-20 carbon atoms and may be substituted with other substituents such as lower alkyl group and may also contain an unsaturated bond therein. Exemplary amines also include polyoxyalkyleneamines between 100 and 10,000 M.W. For example, suitable amines include polyetheramines such as those available under the tradename Jeffamine® from Huntsman. Exemplary amines may be monoamines, diamines, or triamines. Suitable amines may be reacted with the DMC/methanol mixture to form carbamides such as urea.

A catalyst may be used to facilitate the reaction. Any suitable base catalyst known to a person of ordinary skill may be used. Exemplary catalysts include alkali metal carbonate, alkali metal hydroxide, alkali alkoxide, alkaline earth metal carbonate, alkaline earth metal hydroxide, alkaline earth metal alkoxide. For example, the catalyst may be sodium carbonate.

For the reaction, the weight ratio of the alcohol or amine to the DMC/methanol mixture is between about 0.25 and 10; preferably, between 0.5 and 6; and more preferably, between 1 and 4. The reaction may be performed at a temperature between about 25° C. and 200° C. and a pressure range between 0.1 psia and 1,000 psia. The reaction may be performed in a batch or continuous process as is known to a person of ordinary skill. In one embodiment, the reaction is performed in a batch reactor coupled directly or indirectly to a distillation column.

In one embodiment, the DMC/methanol mixture is reacted with glycerine in the presence of a base catalyst such as sodium carbonate in a reactor connected to a distillation column. The reactor and column do not have to be physically connected, but it is more efficient to do so. The reaction is allowed to proceed to equilibrium. Some of the DMC reacts with the glycerine to form glycerine carbonate. However, some of the DMC and glycerine remain unreacted. The lighter components, including DMC and methanol, are removed by distillation, flash distillation, stripping, or any known suitable method. The bottom product mixture includes the desired glycerine carbonate, unreacted glycerine, and some methanol and DMC. For example, the glycerine carbonate may be present in the bottom product mixture in an amount between 10% and 65% by weight or between 20% and 35% by weight. After stripping, the bottom product mixture includes 10% or less by weight of DMC or methanol; preferably, 5% or less by weight of DMC or methanol; and more preferably, 2% or less by weight of DMC or methanol.

In another embodiment, the bottom product mixture may optionally be processed further to obtain a better yield. In this respect, additional DMC/methanol mixture is introduced into the bottom product mixture to react with the remaining glycerine. The second reaction may take place in the same reactor where the first reaction occurred. However, it is contemplated that the second reaction may alternatively take place in another reactor. This second reaction is allowed to proceed to equilibrium. At the end of the reaction, it is possible that the desired glycerine conversion has not been reached. The lighter components, including DMC and methanol, are removed by distillation, flash distillation, stripping, or any known suitable method. The bottom product mixture from the second reaction includes a higher percentage of the glycerine carbonate and less unreacted glycerine. For example, the glycerine carbonate may be present in an amount between 15% and 85% by weight of the second bottom product mixture or between 25% and 60% by weight of the second bottom product mixture. In one embodiment, the bottom product mixture includes 10% or less by weight of DMC or methanol; preferably, 5% or less by weight of DMC or methanol; and more preferably, 2% or less by weight of DMC or methanol.

The reaction may be repeated until the bottom product mixture contains the desired amount of glycerine carbonate. For example, a third reaction may be performed by reacting the second bottom product mixture with additional DMC/methanol mixture. After the reaction and stripping the lighter components, the amount of glycerine carbonate in the third bottom product mixture may increase to between 35% and 95% by weight or between 45% and 85% by weight. In yet another embodiment, a fourth reaction may be performed by reacting the third bottom product mixture with additional DMC/methanol mixture to further increase the amount of glycerine conversion. It must be noted that the DMC/methanol mixture used in the reactions, such as the first, second, third, or fourth reactions, may include the same or different concentrations of DMC by weight in the DMC/methanol mixture. For example, the DMC/methanol composition for any of the reactions may include about 20% to 80% by weight of DMC; preferably about 30% to 70% by weight of DMC; more preferably about 40% to 50% by weight of DMC.

In yet another embodiment, the bottom product mixture may optionally be processed further to convert more of the glycerine. The bottom product mixture from any one of the first, second, third, fourth, or additional reactions may be reacted with pure DMC or at least 95% DMC by weight of the DMC containing mixture, and preferably, at least 98% DMC by weight, to increase the glycerine conversion. After stripping the lighter components such as the DMC and methanol, the glycerine carbonate in the bottom product mixture may be at least 85% by weight; preferably, at least 90% by weight. It is contemplated that additional reactions with a DMC mixture having at least 95% by weight of DMC may be performed to obtain a higher percentage of glycerine carbonate, such as at least 95% by weight.

EXAMPLE 1

The DMC/methanol mixture (44.8% DMC by wt.) was reacted with different amounts of glycerine at 70° C. Significant amount of DMC in the mixture was converted into glycerine carbonate ("GC"). The light component methanol and some residual DMC was stripped and condensed. The bottom product mixture contains glycerine and glycerine carbonate. The bottom product mixture was used to react with pure DMC to make high quality glycerine carbonate. When glycerine and DMC/methanol mixture were reacted in 2:1 ratio by weight percentage, >85% of the DMC in the DMC/methanol mixture was converted into high value GC.

A series of weight ratio experiments were completed to see the effect on DMC recovery (conversion) and product purity as seen in FIG. 1 below.

EXAMPLE 2

In a first reaction, 3400 kg of glycerine is reacted with 3200 kg of 43.9% DMC of a DMC/methanol mixture in the presence of a base catalyst, anhydrous sodium carbonate at 70° C. and atmospheric pressure. After stripping the lighter components, the first bottom product included 3892 kg of 63.9% glycerine, 30.2% glycerine carbonate, and 3.95% methanol. In a second reaction, 3200 kg of 44.9% DMC of a DMC/methanol mixture was added to the first bottom product mixture. After stripping, the second bottom product mixture included 4112 kg of 42.9% glycerine, 53.1% glycerine carbonate, 4.3% methanol, and 0.27% DMC. In a third reaction, 3762 kg of 48% DMC of a DMC/methanol mixture was added to the second bottom product mixture. After stripping, the third bottom product included 4222 kg of 36.7% glycerine, 58.4% glycerine carbonate, 4.24% methanol, and 0.26% DMC. In a fourth reaction, 2130 kg of pure DMC was added to the third bottom product mixture. After stripping, the fourth bottom product included 4557 kg of 3.67% glycerine, 93.8% glycerine carbonate, 1.35% methanol, and 0.91% DMC. In a fifth reaction, 250 kg of pure DMC was added to the fourth bottom product mixture. After stripping, the fifth bottom product included 4428 kg of 1.77% glycerine, 96.3% glycerine carbonate, methanol below detection and 0.045% DMC.

While the foregoing is directed to embodiments of the present invention, other and further embodiments of the invention may be devised without departing from the basic scope thereof, and the scope thereof is determined by the claims that follow.

The invention claimed is:

1. A method of producing a carbonate comprising:
    supplying a dimethyl carbonate ("DMC") and methanol composition having 20% to 80% DMC by weight into a reactor;
    mixing the DMC and methanol composition having 20% to 80% DMC by weight with an alcohol selected from an aliphatic alcohol consisting of 2 to 15 carbon atoms and an aromatic alcohol consisting of 6 to 15 carbon atoms in the reactor, wherein the weight ratio of the alcohol to the DMC and methanol composition is between about 0.25 and 10;
    reacting the DMC with the alcohol to form a carbonate product; and
    removing at least a portion of unreacted DMC and methanol, thereby forming a product composition containing the carbonate product and less than 10% by weight of unreacted DMC or methanol.

2. The method of claim 1, further comprising supplying and mixing an additional amount of DMC and methanol composition having 20% to 80% DMC by weight with the product composition; and
    removing at least a portion of unreacted DMC and methanol, thereby forming a second product composition having less than 10% by weight of unreacted DMC or methanol.

3. The method of claim 2, the method further comprising mixing a sufficient amount of an at least 95% by weight of DMC composition with the second product composition to form a third product composition containing at least 90% by weight of the carbonate product.

4. The method of claim 3, further comprising repeating at least one time the steps of mixing additional amount of DMC and methanol composition before performing the step of mixing the at least 95% by weight of DMC composition.

5. The method of claim 4, wherein after each step of removing a portion of unreacted DMC and methanol, the respective product composition includes less than 5% by weight of unreacted DMC or methanol.

6. The method of claim 2, wherein the additional amount of DMC and methanol composition has a different concentration of DMC by weight than the DMC and methanol composition mixed with the alcohol.

7. The method of claim 1, wherein the alcohol is glycerine.

8. The method of claim 1, wherein the alcohol is one of phenol, ethanol, ethylene glycol, 1, 2 butylene glycol, n-butanol and 1,2 propylene glycol.

9. The method of claim 1, wherein the DMC and methanol composition contains 30% to 70% DMC by weight.

10. The method of claim 1, wherein the DMC and methanol composition contains 40% to 50% DMC by weight.

11. The method of claim 1, wherein the weight ratio of alcohol to the DMC and methanol composition is between about 0.5 and 6.

12. The method of claim 1, wherein the weight ratio of alcohol to the DMC and methanol composition is between about 1 and 4.

13. The method of claim 12, wherein the DMC and methanol composition contains 40% to 50% DMC by weight.

14. The method of claim 1, wherein the DMC and methanol composition comprises an azeotropic composition.

15. The method of claim 12, wherein the DMC and methanol composition contains 40% to 50% DMC by weight.

16. The method of claim 1, wherein the unreacted DMC or methanol is removed using distillation, flash distillation, or stripping.

17. The method of claim 1, wherein the reaction between the DMC and the alcohol is allowed to proceed to equilibrium before removing at least a portion of unreacted DMC and methanol.

18. A method of producing a glycerine carbonate comprising:
   supplying a dimethyl carbonate ("DMC") and methanol composition having 20% to 80% DMC by weight as a reactant;
   mixing the reactant with a glycerine, wherein the weight ratio of the glycerine to the DMC and methanol composition is between about 0.25 and 10;
   reacting the DMC with the glycerine to form glycerine carbonate; and
   removing at least a portion of unreacted and methanol, thereby forming a product composition containing the glycerine carbonate and 10% or less by weight of DMC or methanol.

19. The method of claim 18, further comprising performing at least one iteration of supplying and mixing an additional amount of DMC and methanol composition having 20% to 80% DMC by weight with the product composition; and
   removing at least a portion of unreacted DMC and methanol, thereby forming a second product composition having less than 10% by weight of unreacted DMC or methanol.

20. The method of claim 19, the method further comprising mixing an at least 95% by weight of DMC composition with the second product composition to form a third product composition containing at least 90% by weight of the carbonate product.

21. The method of claim 18, wherein the reaction between the DMC and the glycerine is allowed to proceed to equilibrium before removing at least a portion of unreacted DMC and methanol.

22. The method of claim 18, wherein the weight ratio of glycerine to the DMC and methanol composition is between about 1 and 4.

* * * * *